US 8,494,802 B2

(12) United States Patent
Chen et al.

(10) Patent No.: US 8,494,802 B2
(45) Date of Patent: Jul. 23, 2013

(54) COMPUTER-IMPLEMENTED METHODS, COMPUTER-READABLE MEDIA, AND SYSTEMS FOR DETERMINING ONE OR MORE CHARACTERISTICS OF A WAFER

(75) Inventors: Haiguang Chen, Mountain View, CA (US); Daniel Kavaldjiev, San Jose, CA (US); Louis Vintro, Portland, OR (US); George Kren, Los Altos Hills, CA (US)

(73) Assignee: KLA-Tencor Corp., Milpitas, CA (US)

( * ) Notice: Subject to any disclaimer, the term of this patent is extended or adjusted under 35 U.S.C. 154(b) by 190 days.

(21) Appl. No.: 13/000,013

(22) PCT Filed: Jun. 19, 2009

(86) PCT No.: PCT/US2009/047932
§ 371 (c)(1),
(2), (4) Date: Mar. 13, 2011

(87) PCT Pub. No.: WO2009/155502
PCT Pub. Date: Dec. 23, 2009

(65) Prior Publication Data
US 2011/0196639 A1    Aug. 11, 2011

Related U.S. Application Data

(60) Provisional application No. 61/074,065, filed on Jun. 19, 2008.

(51) Int. Cl.
*G06F 19/00*    (2011.01)
(52) U.S. Cl.
USPC ............ 702/108; 702/40; 702/85; 356/237.1; 356/237.2; 356/237.5; 356/237.6; 438/14; 382/141; 382/145; 324/457

(58) Field of Classification Search
USPC ....... 702/108, 81–84, 117, 40, 85; 356/237.1, 356/237.2, 237.5, 237.6; 438/14; 382/141, 382/145; 324/457
See application file for complete search history.

(56) References Cited

U.S. PATENT DOCUMENTS

| | | | |
|---|---|---|---|
| 4,162,126 A | 7/1979 | Nakagawa et al. |
| 4,410,278 A | 10/1983 | Makihira et al. |
| 4,845,558 A | 7/1989 | Tsai et al. |
| 4,898,471 A | 2/1990 | Vaught et al. |
| 5,027,122 A | 6/1991 | Wieler |
| 5,132,786 A | 7/1992 | Ishiwata |
| 5,355,212 A | 10/1994 | Wells et al. |
| 5,533,387 A | 7/1996 | Aihara et al. |
| 5,555,315 A | 9/1996 | Itakura |

(Continued)

FOREIGN PATENT DOCUMENTS

| | | |
|---|---|---|
| JP | Hei 11-237226 | 8/1999 |
| JP | 2000-002514 | 1/2000 |

(Continued)

OTHER PUBLICATIONS

U.S. Appl. No. 11/855,573, filed Sep. 14, 2007 by Wu et al.

(Continued)

*Primary Examiner* — Carol Tsai
(74) *Attorney, Agent, or Firm* — Ann Marie Mewherter (57) ABSTRACT

Computer-implemented methods, computer-readable media, and systems for determining one or more characteristics of a wafer are provided.

19 Claims, 5 Drawing Sheets

U.S. PATENT DOCUMENTS

| | | | |
|---|---|---|---|
| 5,608,453 A | 3/1997 | Gerber et al. | |
| 5,625,451 A | 4/1997 | Schiff et al. | |
| 5,661,408 A | 8/1997 | Kamieniecki et al. | |
| 5,712,701 A | 1/1998 | Clementi et al. | |
| 5,813,333 A | 9/1998 | Ohno | |
| 5,877,860 A | 3/1999 | Borden | |
| 5,903,342 A | 5/1999 | Yatsugake et al. | |
| 5,909,276 A | 6/1999 | Kinney et al. | |
| 5,991,699 A | 11/1999 | Kulkarni et al. | |
| 6,025,206 A | 2/2000 | Chen et al. | |
| 6,118,525 A | 9/2000 | Fossey et al. | |
| 6,157,444 A | 12/2000 | Tomita et al. | |
| 6,171,975 B1 | 1/2001 | Hase et al. | |
| 6,201,601 B1 | 3/2001 | Vaez-Iravani et al. | |
| 6,202,037 B1* | 3/2001 | Hattori et al. | 702/182 |
| 6,265,719 B1 | 7/2001 | Yamazaki et al. | |
| 6,271,916 B1 | 8/2001 | Marxer et al. | |
| 6,538,730 B2 | 3/2003 | Vaez-Iravani et al. | |
| 6,552,337 B1 | 4/2003 | Cho et al. | |
| 6,558,853 B1 | 5/2003 | Kawamura | |
| 6,563,577 B2 | 5/2003 | Oomori et al. | |
| 6,596,553 B1 | 7/2003 | Lin et al. | |
| 6,603,877 B1 | 8/2003 | Bishop | |
| 6,636,031 B1 | 10/2003 | Kenmochi et al. | |
| 6,718,526 B1 | 4/2004 | Eldredge et al. | |
| 6,781,688 B2 | 8/2004 | Kren et al. | |
| 6,794,885 B1 | 9/2004 | Yasumoto | |
| 6,858,859 B2 | 2/2005 | Kusunose | |
| 6,862,096 B2 | 3/2005 | Vaez-Iravani et al. | |
| 6,893,786 B2 | 5/2005 | Baggenstoss | |
| 6,898,305 B2* | 5/2005 | Hiroi et al. | 382/149 |
| 6,917,419 B2 | 7/2005 | Fielden et al. | |
| 6,917,433 B2 | 7/2005 | Levy et al. | |
| 6,919,957 B2 | 7/2005 | Nikoonahad et al. | |
| 7,006,886 B1 | 2/2006 | Huet et al. | |
| 7,038,772 B2* | 5/2006 | Chen et al. | 356/237.2 |
| 7,038,773 B2 | 5/2006 | Kuhlmann et al. | |
| 7,067,819 B2 | 6/2006 | Janik | |
| 7,286,218 B2 | 10/2007 | Tiemeyer et al. | |
| 7,315,642 B2 | 1/2008 | Bartov et al. | |
| 7,339,661 B2 | 3/2008 | Korngut et al. | |
| 7,349,079 B2 | 3/2008 | Zhao et al. | |
| 7,359,052 B2 | 4/2008 | Fielden et al. | |
| 7,369,233 B2 | 5/2008 | Nikoonahad et al. | |
| 7,373,277 B1 | 5/2008 | Wu et al. | |
| 7,417,722 B2 | 8/2008 | Bills et al. | |
| 7,528,944 B2* | 5/2009 | Chen et al. | 356/237.6 |
| 7,570,796 B2 | 8/2009 | Zafar et al. | |
| 7,676,077 B2 | 3/2010 | Kulkarni et al. | |
| 7,747,062 B2* | 6/2010 | Chen et al. | 382/145 |
| 7,751,046 B2 | 7/2010 | Levy et al. | |
| 7,774,153 B1* | 8/2010 | Smith | 702/85 |
| 7,877,722 B2 | 1/2011 | Kulkarni et al. | |
| 7,894,659 B2 | 2/2011 | Chen et al. | |
| 7,904,845 B2 | 3/2011 | Fouquet et al. | |
| 7,912,658 B2* | 3/2011 | Biellak et al. | 702/40 |
| 7,925,072 B2 | 4/2011 | Chen et al. | |
| 8,045,145 B1* | 10/2011 | Bakker et al. | 356/237.2 |
| 8,126,255 B2 | 2/2012 | Bhaskar et al. | |
| 8,194,968 B2 | 6/2012 | Park et al. | |
| 8,269,960 B2 | 9/2012 | Reich et al. | |
| 8,284,394 B2* | 10/2012 | Kirk et al. | 356/237.5 |
| 2002/0042682 A1* | 4/2002 | Yoshitake et al. | 702/35 |
| 2002/0182760 A1 | 12/2002 | Wack et al. | |
| 2003/0011786 A1 | 1/2003 | Levy et al. | |
| 2003/0107736 A1 | 6/2003 | Fujimoto | |
| 2003/0210393 A1 | 11/2003 | Vaez-Iravani et al. | |
| 2003/0228050 A1 | 12/2003 | Geshel et al. | |
| 2004/0066962 A1* | 4/2004 | Sasa et al. | 382/141 |
| 2004/0095575 A1 | 5/2004 | Woo et al. | |
| 2004/0252879 A1 | 12/2004 | Tiemeyer et al. | |
| 2005/0051728 A1 | 3/2005 | Miyauchi | |
| 2005/0094864 A1 | 5/2005 | Xu et al. | |
| 2005/0179910 A1 | 8/2005 | Bartov | |
| 2005/0186670 A1 | 8/2005 | Oh | |
| 2005/0252752 A1 | 11/2005 | Fielden et al. | |
| 2006/0036409 A1* | 2/2006 | Yamaguchi et al. | 702/189 |
| 2006/0062445 A1 | 3/2006 | Verma et al. | |
| 2006/0091332 A1 | 5/2006 | Nishiyama et al. | |
| 2006/0181700 A1 | 8/2006 | Andrews et al. | |
| 2006/0192948 A1 | 8/2006 | Judell et al. | |
| 2006/0192949 A1 | 8/2006 | Bills et al. | |
| 2006/0192950 A1 | 8/2006 | Judell et al. | |
| 2006/0256326 A1 | 11/2006 | Bills et al. | |
| 2006/0290923 A1 | 12/2006 | Nakano et al. | |
| 2007/0024998 A1 | 2/2007 | Bills et al. | |
| 2007/0156379 A1 | 7/2007 | Kulkarni et al. | |
| 2007/0252977 A1 | 11/2007 | Baran et al. | |
| 2007/0288219 A1 | 12/2007 | Zafar et al. | |
| 2008/0004823 A1 | 1/2008 | Matsushita et al. | |
| 2008/0013083 A1* | 1/2008 | Kirk et al. | 356/237.5 |
| 2008/0018887 A1* | 1/2008 | Chen et al. | 356/237.2 |
| 2008/0032429 A1* | 2/2008 | Chen et al. | 438/14 |
| 2008/0059094 A1* | 3/2008 | Shimura et al. | 702/81 |
| 2008/0129988 A1 | 6/2008 | Saito et al. | |
| 2008/0163140 A1 | 7/2008 | Fouquet et al. | |
| 2008/0167829 A1 | 7/2008 | Park et al. | |
| 2008/0205745 A1 | 8/2008 | Chen et al. | |
| 2008/0219545 A1 | 9/2008 | Chen et al. | |
| 2008/0250384 A1 | 10/2008 | Kulkarni et al. | |
| 2009/0037134 A1 | 2/2009 | Kulkarni et al. | |
| 2009/0080759 A1 | 3/2009 | Bhaskar et al. | |
| 2009/0248341 A1* | 10/2009 | Tian et al. | 702/82 |
| 2009/0299655 A1 | 12/2009 | Biellak et al. | |
| 2010/0060888 A1 | 3/2010 | Reich et al. | |
| 2010/0190322 A1 | 7/2010 | Suzuki et al. | |
| 2011/0196639 A1 | 8/2011 | Chen et al. | |
| 2011/0304527 A1 | 12/2011 | Wu et al. | |
| 2013/0035877 A1* | 2/2013 | Kirk et al. | 702/40 |

FOREIGN PATENT DOCUMENTS

| | | |
|---|---|---|
| JP | 2002-257518 | 9/2002 |
| JP | 2003-240713 | 8/2003 |
| JP | 2004-513509 | 4/2004 |
| JP | 2004-524538 | 8/2004 |
| JP | 2008-096430 | 4/2008 |
| KR | 10-1999-0073971 | 10/1999 |
| KR | 10-2001-0001224 | 1/2001 |
| KR | 10-0738809 | 7/2007 |
| WO | 2004/105087 | 12/2004 |
| WO | 2005/090650 | 9/2005 |
| WO | 2006/066135 | 6/2006 |
| WO | 2006/066136 | 6/2006 |
| WO | 2006/066137 | 6/2006 |
| WO | 2006/066138 | 6/2006 |
| WO | 2006/066139 | 6/2006 |
| WO | 2006/066205 | 6/2006 |
| WO | 2006/066206 | 6/2006 |
| WO | 2006/066207 | 6/2006 |
| WO | 2006/066255 | 6/2006 |

OTHER PUBLICATIONS

U.S. Appl. No. 11/855,581, filed Sep. 14, 2007 by Wu et al.

Chen et al. "Laser Scattering Correlation with Polysilicon Surface Roughness and Impact on Electrical Performance," ISSM 2006.

Elson et al. "Relationship of the total integrated scattering from multilayer-coated optics to angle of incidence, polarization, correlation length, and roughness cross-correlation properties," J.M. et al. Applied Optics, 22, 3207 (1983).

Griffith, J.E. et al.; "Characterization of Scanning Probe Tips for Linewidth Measurement," J. Vac. Sci. Technol. B 9(6), Nov./Dec. 1991, pp. 3586-3589.

Holsteynes et al. "The use of unpatterned wafer inspection for immersion lithography defectivity studies." Apr. 2006.

International Application No. PCT/US05/45781 filed on Dec. 12, 2005.

Larson, C. Thomas; "Measuring Haze on Deposited Metals with Light-Scattering-Based Inspection Systems," MICRO (Sep. 1996), pp. 31-38.

Malik, Igor J. et al. "Surface Roughness of Si Wafers: Correlating AFM and Haze Measurements," Semiconductor Silicon/1994: Seventh International Symposium on Silicon Materials Science and Technology, ed. H.R. Huff, W. Bergholz and K. Sumino, The Electrochemical Society, Inc. PV 94-10, Pennington, NJ, 1994, p. 1182.

Marx, Egon et al. "Power spectral densities: A multiple technique study of different Si wafer surfaces," J. Vac. Sci. Technol. B 20(1), Jan./Feb. 2002, pp. 31-41.

McMillan, Wayne; "Surfscan SP2: Enabling Cost-Effective Production and the 65nm Node and Beyond," Yield Management Solutions, Summer 2004, pp. 14-23.

Nemoto et al. "Impact of Silicon Surface Roughness on Device Performance and Novel Roughness Measurement Method," IEEE/SEMI Advanced Semiconductor Manufacturing Conference, 2007.

Scheer, B.W. "Development of a physical haze and microroughness standard," SPIE vol. 2862, pp. 78-95 (1996).

Stover, John C. Optical Scattering: Measurement and Analysis, SPIE Optical Engineering Press, Bellingham, WA (1995).

International Search Report and Written Opinion for PCT/US2009/047932 mailed Jan. 20, 2010.

International Preliminary Report on Patentability for PCT/US2009/047932 mailed Jan. 6, 2011.

* cited by examiner

COMPUTER-IMPLEMENTED METHODS, COMPUTER-READABLE MEDIA, AND SYSTEMS FOR DETERMINING ONE OR MORE CHARACTERISTICS OF A WAFER

CROSS-REFERENCE TO RELATED APPLICATIONS

This application is a National Stage application of International Application No. PCT/US09/47932 filed Jun. 19, 2009, which claims priority to U.S. Provisional Application No. 61/074,065 entitled "Computer-Implemented Methods, Computer-Readable Media, and Systems for Determining One or More Characteristics of a Wafer," filed Jun. 19, 2008, which is incorporated by reference as if fully set forth herein.

BACKGROUND OF THE INVENTION

1. Field of the Invention

This invention generally relates to computer-implemented methods, computer-readable media, and systems for determining one or more characteristics of a wafer.

2. Description of the Related Art

The following description and examples are not admitted to be prior art by virtue of their inclusion in this section.

Metrology processes are performed at various steps during a semiconductor manufacturing process to monitor and control the process. Metrology processes are used to measure characteristics of wafers that generally cannot be determined using inspection tools. There are, however, a number of disadvantages to using metrology processes and tools for process monitoring and control applications. For example, most metrology tools are relatively slow. Therefore, metrology processes are often performed at one location or a limited number of locations on wafers. However, metrology characteristic(s) can vary across the surface of the wafers. As such, metrology measurements performed at one location or a limited number of locations on a wafer may not provide sufficient information about the characteristic(s) of the wafers such that processes can be accurately monitored and controlled. Furthermore, using metrology tools to measure characteristics across the wafer for inline monitoring and control applications is not feasible. In particular, metrology measurements performed by currently available metrology tools are not suitable for high sampling of wafers for inline monitoring since the measurements will impact cycle time in production.

Attempts have been made to try to use inspection systems to determine metrology-like characteristics of wafers. For example, typically, inspection systems are configured with a number of collectors or channels. Each of these collectors or channels is able to capture multiple characteristics of the inspection surface. In the above described method, surface anomalies or features are extracted and then compared with similar features from separate signals. Therefore, currently used detection methods disadvantageously have to discriminate against common background and nuisance features to extract the surface anomalies or features of interest.

Accordingly, it would be advantageous to suppress background and nuisance surface features in output generated by an inspection system for a wafer before the output is used to determine one or more characteristics of the wafer.

SUMMARY OF THE INVENTION

The following description of various computer-implemented method, computer-readable medium and system embodiments is not to be construed in any way as limiting the subject matter of the appended claims.

One embodiment relates to a computer-implemented method for determining one or more characteristics of a wafer. The method includes using a computer system to perform the following steps of the method. The method includes acquiring output generated for the wafer by an inspection system. The method also includes separately altering the output generated for different locations on the wafer using a reference corresponding to the different locations on the wafer. The output that is altered includes output that does not correspond to defects on the wafer. In addition, the method includes determining one or more characteristics of the wafer using the altered output.

Each of the steps of the computer-implemented method may be further performed as described herein. In addition, the computer-implemented method may include any other step(s) of any other method(s) described herein. Furthermore, the computer-implemented method may be performed by any of the systems described herein.

Another embodiment relates to a computer-readable medium storing program instructions executable on a computer system for performing the computer-implemented method described above. Each of the steps of the computer-implemented method may be further performed as described herein. In addition, the computer-implemented method may include any other step(s) of any other method(s) described herein. The computer-readable medium may be further configured as described herein.

An additional embodiment relates to a system configured to determine one or more characteristics of a wafer. The system includes an inspection subsystem configured to generate output for the wafer. The system also includes a computer subsystem configured to acquire the output. The computer subsystem is also configured to separately alter the output generated for different locations on the wafer using a reference corresponding to the different locations on the wafer. The output that is altered includes output that does not correspond to defects on the wafer. In addition, the computer subsystem is configured to determine one or more characteristics of the wafer using the altered output. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements.

One embodiment relates to a computer-implemented method for determining one or more characteristics of a wafer. The method includes performing some or all of the steps of the method using a computer system, which may be configured as described herein. The method includes acquiring output generated for the wafer by an inspection system. The output may be responsive to light scattered and/or reflected from the wafer and detected by the inspection system. The acquired output may include signals, original scan signals, data, transformed measurement data, image data, images, reconstructed images, etc.

Figure 1:
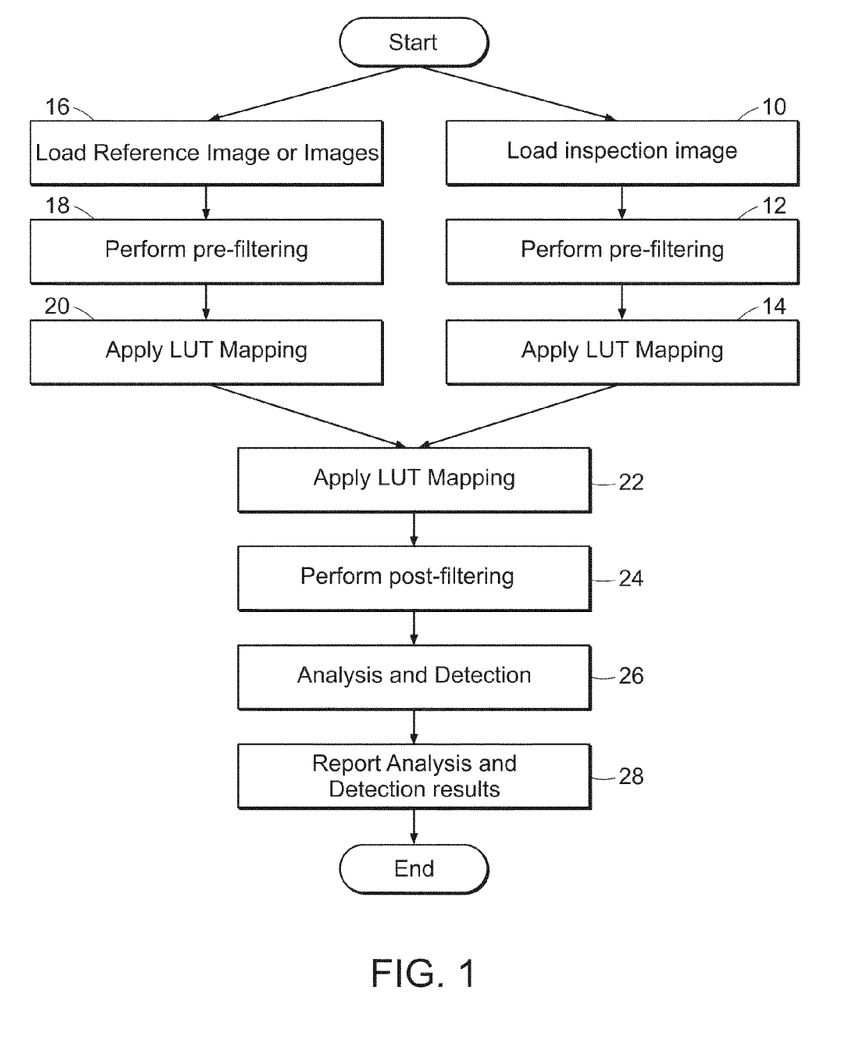
FIG. 1 is a flow chart illustrating one embodiment of a computer-implemented method for determining one or more characteristics of a wafer.

Acquiring the output generated for the wafer by the inspection system may include using the inspection system to scan light over the wafer and to generate output responsive to light scattered and/or reflected from the wafer detected by the inspection system during scanning. However, acquiring the output may include acquiring the output from a computer-readable medium in which the output has been stored (e.g., by the inspection system). For example, FIG. 1 illustrates one embodiment of a computer-implemented method for determining one or more characteristics of a wafer. In particular, FIG. 1 is a processing flow chart for defect and feature detection in differential haze image measurements and other image measurements. In this method, acquiring the output includes loading an inspection image, as shown in step 10.

The method also includes separately altering the output generated for different locations on the wafer using a reference corresponding to the different locations on the wafer. Separately altering the output may essentially compare the output generated for the wafer with the reference at corresponding locations on the wafer. Separately altering the output may be performed using a mathematical operator, which may vary depending on the specific use case or application in which the method is being used. For example, the mathematical operator may include subtraction (difference), division, sum, or some combination thereof. In addition, if the output includes an inspection image, the inspection image and a reference image can have different spatial resolutions and can be compared using multi-resolution algorithm(s).

The output may include discrete values generated for different locations on the wafer. The different locations may correspond to different "inspection points" on the wafer. In this manner, the different locations may correspond to each location on the wafer at which a "measurement" is performed by the inspection system. In addition, the reference may be created, stored, etc. as a function of location on the wafer. In other words, the reference may include discrete reference values corresponding to different locations on the wafer. In this manner, different values of the reference corresponding to different locations on the wafer can be separately used to alter the output generated at the different locations. As such, separately altering the output may include altering the output on a location-by-location basis (or an inspection point-by-inspection point basis).

The output that is altered includes output that does not correspond to defects on the wafer. In this manner, the output that is altered may include background signals generated by the inspection system. For example, the output that is altered may include output responsive to light scattered from the wafer surface(s) and/or light scattered from the wafer due to pattern noise. The output that is altered may also include output that does correspond to detects on the wafer. For example, the output that is altered may include all of the output generated for the wafer by the inspection system regardless of whether the output corresponds to defects on the wafer. In other words, separately altering the output may be performed indiscriminately with respect to the output itself.

The method may also include storing all of the output generated by the inspection system for the wafer and separately altering all or some of the stored output. The method may also include storing all of the separately altered output. The method may include storing the output and/or the altered output using a system such as that described in commonly owned U.S. patent application Ser. No. 12/234,201 by Bhaskar et al. filed Sep. 19, 2008, published as U.S. Patent Application Publication No. 2009/0080759 on Mar. 26, 2009, which is incorporated by reference as if fully set forth herein. All of the stored altered output may be used to perform any of the steps described herein and any step(s) of any method(s) described in the above-referenced patent application.

In one embodiment, separately altering the output is performed prior to detecting the defects on the wafer (i.e., prior to processing the output for defect detection purposes). However, the output can be pre-processed before the output is separately altered. The type of pre-processing can be different for each inspection signal. For example, as shown in FIG. 1, the method may include performing pre-filtering, as shown in step 12, on the loaded inspection image to enhance some signal features and to reduce inspection system artifacts in the inspection image. In addition, as shown in FIG. 1, the method may include applying look up table (LUT) mapping, as shown in step 14, to the pre-filtered inspection image. Applying LUT mapping may include applying signal mapping to the inspection image using LUTs in the inspection system recipe. The mapping function may be linear or non-linear depending on the application.

Similar functions may be performed on the reference prior to separately altering the output using the reference. For example, as shown in Fig. 1, the method may include loading a reference image or images, as shown in step 16. The method may also include performing pre-filtering, as shown in step 18, on the loaded reference image or images to enhance some signal features and to reduce inspection system artifacts in the reference image or images. In addition, the method may include applying LUT mapping as described herein, as shown in step 20, to the pre-filtered reference image or images. The mapping function may be linear or non-linear depending on the application.

After the functions described above are performed, the method includes separately altering the inspection image using the reference. For example, the LUT mapped inspection image may be compared to the LUT mapped reference image(s) thereby producing the altered output. This step may include performing a signal comparison using user-selected method(s), such as subtraction or division, to generate the resulting altered inspection image. Functions such as those described above may also be performed on the altered inspection image. For example, the method may include applying LUT mapping, as shown in step 22, to the altered inspection image. In addition, the method may include performing post-filtering, as shown in step 24, on the LUT mapped altered inspection image to enhance the signal features.

In one embodiment, the inspection system generates the output for the wafer by scanning the wafer during an inspection process. The inspection system may generate different output during the scanning (e.g., output simultaneously and/or sequentially generated by different channels or different detection subsystems of the inspection system). The output that is altered may include only a portion of the output generated by scanning the wafer. For example, the output that is altered may include only the output generated by one channel or one detection subsystem. However, the output that is altered may include output generated by more than one channel or detection subsystem. In such instances, the output generated by the different channels or detection subsystems may be separately altered using the same reference or different references as described herein (e.g., on a location-by-location basis). For example, the output generated by a first channel may be separately altered using a first reference, and the output generated by a second channel may be separately altered using a second reference.

In one embodiment, the reference is created from additional output generated by scanning the wafer with the inspection system during the inspection process. For example, the reference may include background signals from the same measurement performed for the wafer. In one such example, the reference may be a reference image from one or more different data acquisition channels for the same wafer. In particular, the output that is altered may include output generated by one channel, and the reference may include or be created from output generated by a different channel. In this manner, separately altering the output may include a channel-to-channel comparison for a single wafer (e.g., a normal-wide channel (i.e., a channel that utilizes normal or near normal illumination and wide scattering angle collection) vs. an oblique-wide channel (i.e., a channel that utilizes oblique illumination and wide scattering angle collection)). In addition, separately altering the output may include performing a comparison of different output for the same wafer generated in different optical modes. For example, the reference and the output (e.g., an inspection image) can be generated by different optical configurations of the inspection system defined by illumination angle, illumination polarization, illumination wavelength(s), collection angles, collection polarization, collection wavelength(s), etc. In this manner, separately altering the output may include performing a differential comparison of the output with background signals from the same measurement (i.e., a single measurement of a single wafer). In this manner, the output that is separately altered and the output used to create the reference may be generated simultaneously or during the same inspection process. The reference may be created from the additional output by simply storing the additional output or by performing one or more functions on the additional output.

In another embodiment, the reference is created from additional output generated by scanning the wafer with the inspection system or a different inspection system during a different process. In this manner, the reference may be created from a separate measurement of a single wafer. For example, the output that is altered and the output used to create the reference may be generated during different inspection processes, one performed before a fabrication process and another performed after the fabrication process. In one such example, the reference may include background signals from a separate measurement of the same wafer. In one such example, one measurement may be a map of output generated for the wafer before a process, and the separate measurement may be a map of output generated for the same wafer after a process. For such measurements, separately altering the output may include subtracting the post-process map from the pre-process map. In addition, separately altering the output may include performing a comparison of different measurements of the same wafer performed at different points in a wafer processing sequence or at different points in time (e.g., before and after one or more process steps) using the same or different optical configurations supported by the inspection system. In an additional example, one measurement may be a map of output generated for a front side of the wafer, and the separate measurement may be a map of output generated for a back side of the same wafer in the case of double sided polished wafers. For such measurements, separately altering the output may include subtracting the back side map from the front side map. In addition, separately altering the output may include performing a comparison of different measurements of the same wafer performed on different sides of the wafer (e.g., front side and back side). In this manner, separately altering the output may include performing a differential comparison with background signals from a separate measurement. In other words, the altered output may be produced using multiple measurements of a single wafer. The different inspection systems may be different inspection systems that have the same configuration (e.g., the same make and model) or different inspection systems that have different configurations.

In an additional embodiment, the reference is created from additional output generated by scanning a different wafer with the inspection system or a different inspection system. As such, separately altering the output may include performing a wafer-to-wafer comparison. For example, the reference may include background signals from a separate measurement performed on a different wafer. In this manner, separately altering the output may include performing a differential comparison with background signals from a separate measurement performed on a different wafer. In addition, separately altering the output may include performing a comparison of a measurement of a wafer with a reference image (which may or may not be stored in a database) of a nominal wafer. As such, the altered output may be produced using multiple measurements of different wafers.

In one such embodiment, the wafer and the different wafer are in the same lot. In this manner, separately altering the output may include performing a wafer-to-wafer comparison within a lot (e.g., output for a wafer in slot #N−(output for wafer in slot #N−1+output for wafer in slot #N+1)/2). In a similar manner, separately altering the output may include performing a comparison of a measurement of a wafer with images of other wafer(s) from the same lot. The additional output may include output corresponding to the same measurements that were performed to generate the output being altered.

In another such embodiment, the wafer and the different wafer are in different lots. For example, separately altering the output may include performing a comparison of a measurement of a wafer with images of other wafer(s) from a different nominal lot. The output and the additional output may be generated in different inspection processes. For example, output for the wafer and the different wafer may be generated by the same inspection system or different inspection systems in different inspection processes. In addition, the additional output may include output corresponding to the same measurements that were performed to generate the output being altered.

As described above, the output generated for the wafer may be pre-processed before the output is separately altered. One or more other functions may be performed on the output prior to separately altering the output. For example, the method may include determining a derivative of the output. The derivative may be a second derivative. In one such embodiment, the reference includes a derivative of different output generated by scanning the wafer or a different wafer with the inspection system or a different inspection system. The derivative of the different output may be a second derivative. The derivative of the output may be the same derivative as the derivative of the different output included in the reference.

In one such embodiment, separately altering the output includes separately altering the derivative of the output generated for the different locations using the derivative of the different output corresponding to the different locations. In this manner, the differential comparison can be performed on differential data (e.g., on a second derivative data map for the wafer). Separately altering the derivative of the output using such a reference may otherwise be performed as described herein.

In one embodiment, the reference is created by performing a function on data acquired from a computer-readable medium. Such a function may include synthesizing the reference from the data using a synthesis method such as any local or global statistic such as mean, simple mean, partial mean, median, rms, etc. and other user-selected statistics for the applications. The partial mean may be determined by skipping the maximum and minimum values of the data sequence and using the remaining data to calculate the partial mean. This process is also called the trimmed mean. However, the partial mean can also be any process in which some data samples are purposely dropped from the mean calculation. In a similar manner, the reference can be synthesized from multiple images based on a global image operation performed on the individual or composite image. For example, the reference can be produced by Zernike interpolation of the median of all reference images. The reference may also include synthesized scattering signals from a database.

In another embodiment, the reference is created by performing a function on data generated for two or more wafers by one or more inspection systems. Performing such a function may include synthesizing the reference from the data using a synthesis method such as simple mean, partial mean, and median. The data may include any output described herein, and the one or more inspection systems may include any of the inspection systems described herein. In this manner, the reference may include synthesized scattering signals from multiple measurements performed on a group of wafers. In another example, the reference may include a synthesized image from a group of wafer images. In a similar manner, separately altering the output may include performing a comparison of a measurement of a wafer with a synthesized image from a database of images (e.g., an average of several wafer images). The data that is synthesized may be acquired from a computer-readable medium.

In another embodiment, the reference includes a map of reference values corresponding to the different locations on the wafer. The values in the map can be the result of a measurement or computation. In one such embodiment, the output generated for the wafer may also include a map (an "inspection map") of values corresponding to the different locations on the wafer. In this manner, separately altering the output may include a single measurement of the wafer vs. the reference (e.g., inspection map-reference map).

In some embodiments, the reference may be user-selected or created based on output selected by the user and/or using operations selected by the user. For example, the method may include a tile (e.g., image tile) selection process for reference (e.g., reference image) generation. The file selection process may include prompting or allowing a user to select a file directory. The file selection process may include displaying the names of all files in a selected directory so that the user can choose one or more files in the directory for reference (e.g., reference image) generation.

Figure 2:
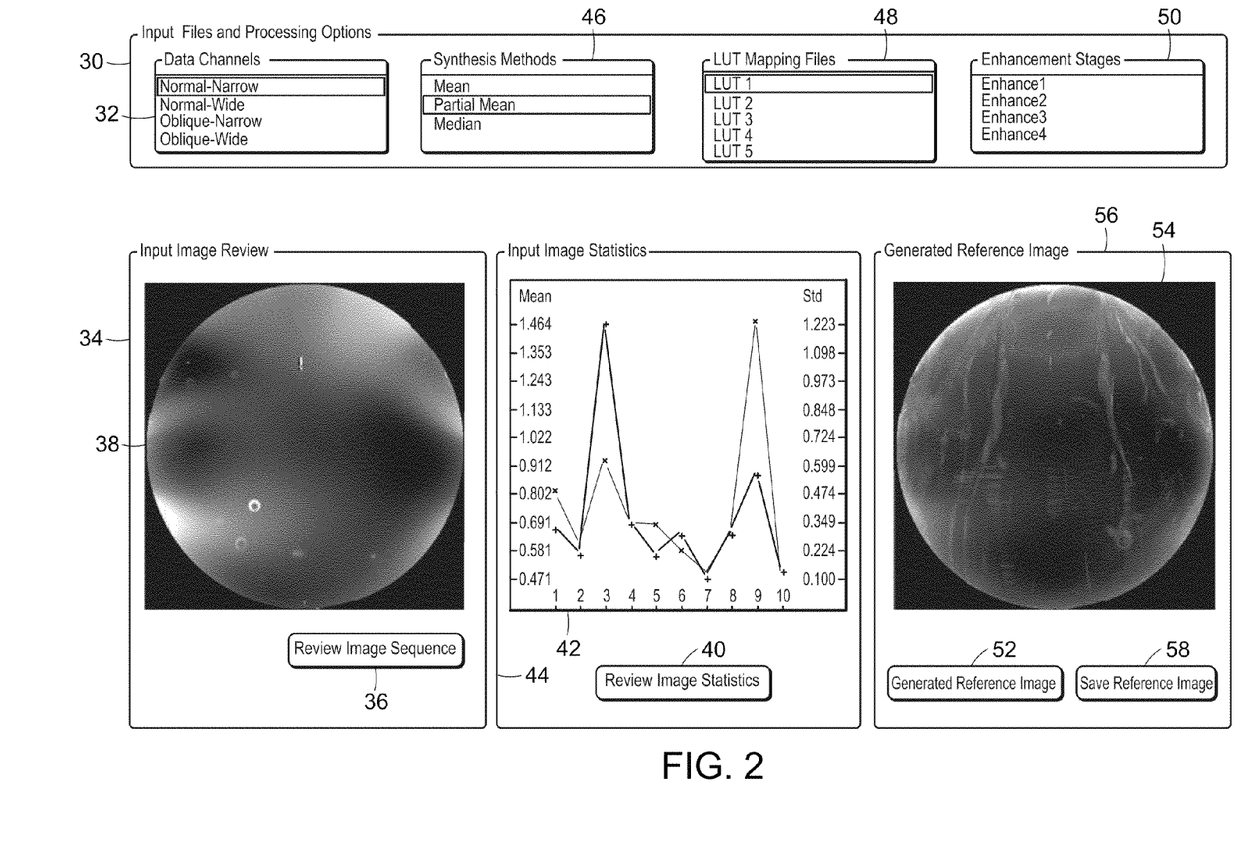
FIG. 2 is a screenshot illustrating one example of output for a wafer and one example of a reference that may be created by the embodiments described herein using the output shown in FIG. 2.

FIG. 2 is a screenshot illustrating one example of output generated for a wafer by an inspection system that may be used to create a reference and one example of a reference that may be created by the embodiments described herein using that output. In this manner, FIG. 2 shows one implementation of defect and feature detection differential haze image measurements and other image measurements. In addition, FIG. 2 shows one example of an image sequence review and reference image generation control page.

After files for reference generation have been selected, a user or the computer-implemented method can move to this reference generation stage. As shown in FIG. 2, in Input Files and Processing Options section 30, the user can select one or more data channels 32 such as normal-narrow (i.e., a channel that utilizes normal or near normal illumination and narrow scattering angle collection), normal-wide, oblique-narrow (i.e., a channel that utilizes oblique illumination and narrow scattering angle collection), and oblique-wide, or any other customer channels defined in the inspection recipe. In Input Image Review section 34, the user can preview the image sequence of the selected image files to check the image properties visually. For example, if the user clicks on Review Image Sequence button 36, review images may be sequentially displayed in window 38.

The user can also review statistics of the image sequence. For example, if the user clicks on Review Image Statistics button 40, statistics of the image sequence may be displayed in window 42 in Input Image Statistics section 44. As shown in FIG. 2, the image mean and standard deviation may be computed and displayed graphically in a plot. More image information can be computed for the automatic image file selection.

The user can also choose different synthesis methods for the reference image generation. For example, as shown in Synthesis Methods section 46, three options for different synthesis methods include the simple mean, partial mean, and median. The user may also select an LUT mapping file in LUT Mapping Files section 48. The images may first be mapped using the selected LUT mapping file to obtain different presentations. Various image enhancement stages may be performed for feature enhancement and artifact reduction. The user may also select an enhancement stage in Enhancement Stages section 50.

The reference image may then be generated and saved into a specific format. For example, if the user clicks on Generate Reference Image button 52, the reference image may be generated. The generated reference image may be displayed in window 54 of Generated Reference Image section 56. In addition, if the user clicks on Save Reference Image button 58, the reference image may be saved. The generated reference image can also be passed to the feature analysis and defect detection stage of the method.

In one embodiment, the altered output includes a map of values corresponding to the different locations on the wafer.

For example, the altered output may include a differential comparison map that is generated by comparing the data from different input signals at each inspection point on the wafer. In this manner, the altered output may include a location-by-location or point-by-point differential map.

In some embodiments, separately altering the output suppresses background and surface features in the output. For example, separately altering the output may result in nuisance suppression and common mode elimination (e.g., by computing the location-by-location or point-by-point differential map from a single measurement or multiple measurements of a single wafer or multiple wafers). In addition, the specific comparison operator to be implemented for a particular use case may be selected to suppress common background and nuisance features (i.e., background and nuisance features that are common to the output generated for the wafer and the output used to create the reference). In this manner, the altered output will advantageously have higher signal-to-noise ratios for defects and "real surface features" or surface features of interest compared to the output generated for the wafer by the inspection system.

The method also includes determining one or more characteristics of the wafer using the altered output. Determining the one or more characteristics may include performing surface anomaly detection/analysis/extraction on the altered output. For example, the method shown in FIG. 1 includes analysis and detection, as shown in step 26, of the post-filtered altered output. The analysis and detection may include signal analysis and feature detection.

Figure 3:
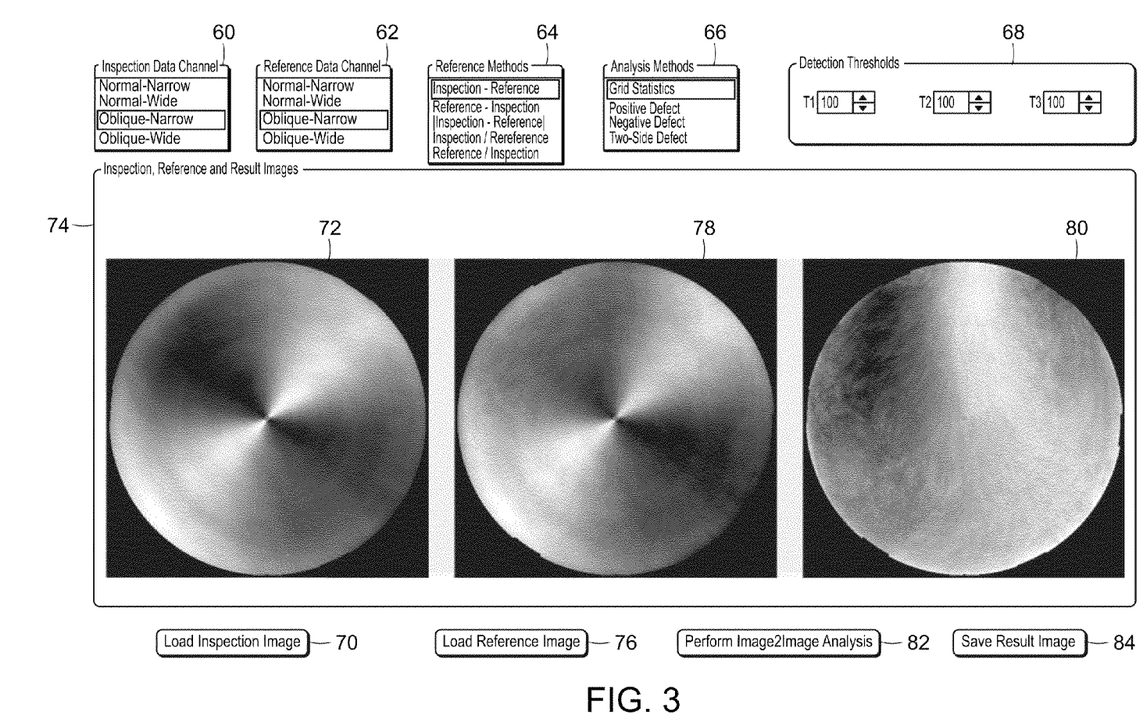
FIG. 3 is a screenshot illustrating one example of altered output that may be generated by the embodiments described herein using the examples of the output and reference shown in FIG. 3.

FIG. 3 is a screenshot illustrating one example of output generated for a wafer by an inspection system, one example of a reference that may be used in the embodiments described herein, and one example of altered output that may be generated by the embodiments described herein. In this manner, FIG. 3 shows one implementation of defect and feature detection in differential haze image measurements and other image measurements. In addition, FIG. 3 shows one example of an image comparison, feature analysis and defect detection control page.

In Inspection Data Channel section 60, the user can select an inspection data channel, which can be any real channel of the inspection system (e.g., normal-narrow, normal-wide, oblique-narrow, oblique-wide) or customer channel specified in the inspection recipe. In Reference Data Channel section 62, the user can select a reference data channel such as any of those described above. In Reference Methods section 64, the user may select a reference method from several options such as "Inspection-Reference" and "Inspection/Reference."

Figure 3A:
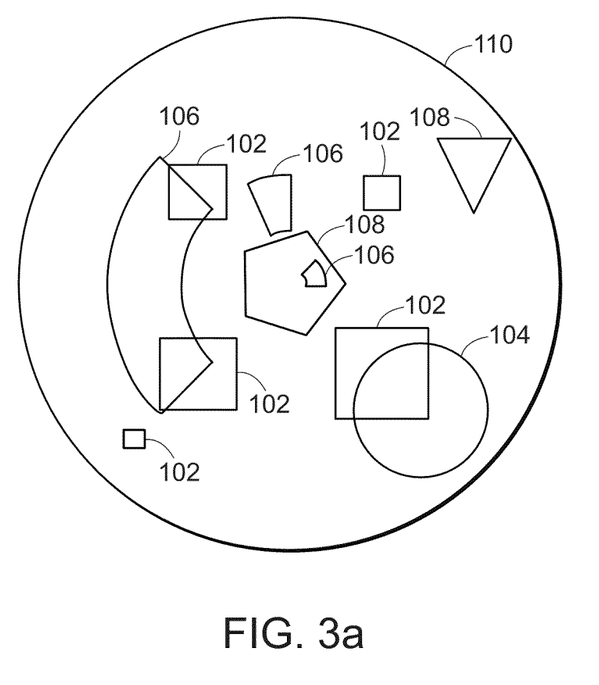
FIG. 3a is a schematic diagram illustrating a plan view of different regions on a wafer for which statistics can be determined by the embodiments described herein.

In Analysis Methods section 66, the user may select the analysis method to apply to the altered output. For example, the user can select to have grid statistics of the comparison result image determined or to have defect detection performed on the resulting image. The grid statistics may include statistics for different regions defined by a grid across the wafer. In addition or alternatively, statistics may be determined for different regions that have different characteristics (e.g., shape, size, etc.), and the regions can be defined in a recipe configured to perform the method. For example, as shown in FIG. 3a, the regions may include rectangular regions 102, disk region 104, polar sector regions 106, polygon regions 108, etc, on wafer 110. As shown in FIG. 3a, some or all of the regions may have various (e.g., irregular) positions on the wafer and various, different dimensions. Certain thresholds may be applied to the resulting image for defect detection. In addition, in Detection Thresholds section 68, the user may select values to be used for one or more thresholds (e.g., threshold 1 (T1), threshold 2 (T2), threshold 3 (T3), etc.) to be applied to the altered output. More analysis and detection methods can be added in this processing stage.

After these processing parameters are set, the user can load the inspection and reference images and perform the image-to-image analysis and defect detection. For example, by clicking on Load Inspection Image button 70, the user can load an inspection image. The loaded inspection image may be displayed in window 72 of Inspection, Reference and Result Images section 74. In addition, by clicking on Load Reference Image button 76, the user can load a reference image. The loaded reference image may be displayed in window 78 of section 74. In the example shown in FIG. 3, the inspection and reference images are images of one wafer before and after one wafer manufacturing stage. In addition, the altered output (e.g., the comparison image) generated using the loaded images may be displayed in window 80 of section 74. In the example shown in FIG. 3, the comparison image is the difference between the inspection and reference images shown in FIG. 3. As shown in the comparison image, the process introduced haze signal change is dramatically revealed. If the user clicks on Perform Image2Image Analysis button 82, image-to-image analysis may be performed on the altered output. The altered output can be saved and/or passed to other processing stages in the method. For example, if the user clicks on Save Result Image button 84, the comparison result image can be saved. In the production mode, the above-described data processing steps can be programmed and run automatically without any user involvement.

In one embodiment, the one or more characteristics include at least one characteristic that is spatially localized in at least one dimension. Such a characteristic can be generally defined as a characteristic of the wafer that is spatially localized in at least one dimension extending in a plane substantially parallel to the upper surface of the wafer (i.e., the x-y plane of the wafer). The spatially localized characteristic may be spatially localized in at least one dimension in that a lateral scale of the characteristic in the at least one dimension is smaller than the width of a point spread function of the inspection system. In this manner, "spatial localization" means on the order of the inspection system optical point spread function width or smaller.

In one embodiment, the defects on the wafer are spatially localized in at leas one dimension. In this manner, a characteristic that is spatially localized in at least one dimension may include the defects that are detected on the wafer. For example, the spatially localized characteristic may be defects such as point defects that are smaller than the width of the point spread function of the inspection system. In addition, the defects may be spatially localized in one or two dimensions. For example, the defects may include particles and defects of varying shapes and sizes such as point defects, particles, pits, scratches, sliptines, missing material, or other features tightly confined in at least one spatial dimension.

Figure 4:
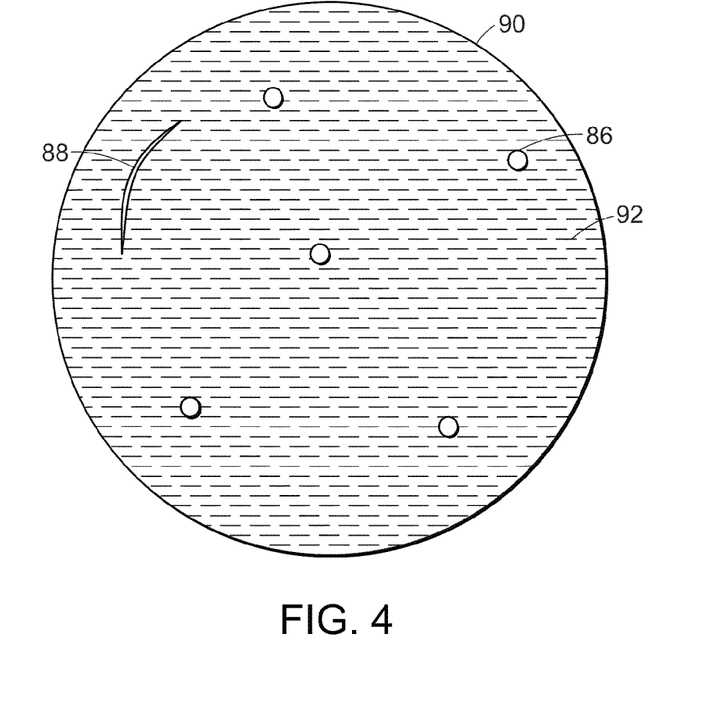
FIG. 4 is a schematic diagram illustrating a plan view of one example of a wafer having different characteristics.

Examples of such particles and defects are shown in FIG. 4. In particular, particles 86 and scratch 88 are located on wafer 90. As shown in FIG. 4, particles 86 are localized in two dimensions, and scratch 88 is localized in one dimension. In other words, particles 86 have strong spatial localization in two dimensions, and scratch 88 has strong spatial localization in one dimension. In this manner, the signals produced by such defects will have strong spatial localization in at least one dimension (e.g., a scratch can be centimeters long but is usually much less than one micron wide). The term "defect" as used herein refers specifically to defects that are spatially localized in at least one dimension as opposed to other characteristics of the wafer described herein (non-spatially localized characteristics) that may render the wafer "defective" but are not themselves considered "defects."

In this manner, the method embodiments described herein may be considered "inspection methods" in that at least one characteristic that can be determined using the altered output may include "defects" that are commonly detected using inspection methods. The defects may include spatially localized defects such as point or extended defects including particles, pits, scratches, stiplines, dimples, micro-scratches, etc. A characteristic that is spatially localized in at least one dimension may also include at least one characteristic of defects that are spatially localized in at least one dimension. For example, the spatially localized characteristic may include any suitable characteristic of the spatially localized defects such as presence, number, types, sizes, and/or spatial locations of the defects. The defects or the characteristics of the defects may be detected and/or determined by applying one or more defect detection algorithms to the altered output. In addition, the method may include performing analysis of structured and/or textured defects. These defects are not spatially localized and may have strong correlation with wafer production.

In one embodiment, the one or more characteristics include at least one characteristic that is not spatially localized in two dimensions. Such a characteristic can be generally defined as a characteristic of the wafer that is not spatially localized in two dimensions extending in a plane substantially parallel to the upper surface of the wafer (i.e., the x-y plane of the wafer). In this manner, a non-spatially localized characteristic does not have strong spatial localization in two dimensions. For example, characteristics of wafers that do not have strong spatial localization in two dimensions include surface roughness or the optical constants and thickness of a deposited film and other examples described herein. In this manner, a non-spatially localized characteristic may include a characteristic with scales of tens of microns to mm to cm rather than what is typically known as "defects." In addition, although values of such non-spatially localized characteristics may render the wafer "defective," the non-spatially localized characteristics themselves are generally not considered "defects" as that term is commonly used. Instead, such non-spatially localized characteristics are generally considered metrology-like characteristics of the wafer, which can generally not be determined using an inspection system.

A non-spatially localized characteristic may include surface roughness, surface roughness variation across the wafer, film thickness, film composition, film residue, one or more pattern dimensions, surface composition, morphology, or morphology changes in the wafer. For example, a non-spatially localized characteristic may include relatively low amplitude, relatively low spatial frequency variations of surface roughness. In addition, the one or more characteristics may include one or more non-spatially localized characteristics that can be determined using output generated by inspection systems such as those described in the patent application by Biellak et al. incorporated by reference below, after that output has been altered as described herein.

A characteristic may also be not spatially localized in two dimensions in that lateral scales of the non-spatially localized characteristic in two dimensions are larger than the width of a point spread function of the inspection system. For example, the non-spatially localized characteristic may be a wafer characteristic that can be measured on a length scale much larger than the width of the inspection system point spread function. In one such example, as shown in FIG. 4, wafer 90 may have surface roughness 92. As shown in FIG. 4, the surface roughness is not spatially localized in two dimensions in that the surface roughness extends across substantially the entire surface of wafer 90. Although a non-spatially localized characteristic may extend across substantially the entire wafer, the non-spatially localized characteristic may not extend across substantially the entire wafer and may still be not spatially localized in two dimensions (e.g., due to the lateral or length scale of the non-spatially localized characteristic as described above).

As described above, the output may include output responsive to background surface scattering or haze. In this manner, the altered output may also be responsive to background surface scattering and haze. As such, at least one non-spatially localized characteristic may be determined using the altered output that is responsive to background surface scattering or haze. In addition, as described above, the output may include output responsive to pattern noise. In this manner, the altered output may also be responsive to pattern noise. As such, at least one non-spatially localized characteristic may be determined using the altered output that is responsive to pattern noise. Therefore, the method embodiments described herein may include performing analysis of non-spatially localized characteristic(s) of the wafer. However, as described further herein, the method embodiments may also include performing analysis of spatially localized defects on the wafer, which is advantageous as described further herein.

In one embodiment, determining the one or more characteristics includes extracting one or more features of the wafer from the altered output. Extracting one or more features of the wafer from the altered output enables more sensitive detection and better extraction of surface features present in the background signal of a wafer inspection system by differential comparison with a background signal from the same measurement or from a separate measurement, or from comparison with a synthesized scattering signal from a database or from multiple measurements from a group of wafers. For example, the method allows for monitoring relatively small changes in the inspection signal on top of relatively large background variations. In this manner, a feature extraction algorithm can be simplified due to the effectively increased signal-to-noise ratio of the altered output compared to the output generated by the inspection system. In some instances, any of the altered output that is determined to correspond to spatially localized defects on the wafer may be eliminated or otherwise removed from the altered output prior to determining the non-spatially localized characteristic of the wafer.

A non-spatially localized characteristic of the wafer may also be determined by haze analysis of the altered output using commercially available software and/or hardware such as the SURF monitor process signature and metrology module and/or the SP2 inspection system, both of which are commercially available from KLA-Tencor, San Jose, Calif. The non-spatially localized characteristic may also be determined using the altered output and systems and methods described in commonly owned U.S. patent application Ser. No. 11/673,150 by Kirk et al. filed Feb. 9, 2007, which published as U.S. Patent Application Publication No. 2008/0013083 on Jan. 17, 2008, and Ser. No. 12/179,260 by Reich et al, filed Jul. 24, 2008, which published on Mar. 11, 2010 as U.S. Patent Application Publication No. 2010/0060888, both of which are incorporated by reference as if fully set forth herein. A non-spatially localized characteristic of the wafer determined using the altered output may also include any non-spatially localized characteristic described in these patent applications.

As described above, the method may include storing all of the altered output for the entire wafer or the entire portion of the wafer that is scanned during the inspection process. In some such cases, the non-spatially localized characteristic may be determined using some or all of the stored altered output. The method may also include determining variation in the non-spatially localized characteristic over the entire wafer, over the entire portion of the water that is scanned, along one direction of the wafer, or in different regions of the wafer as a function of position across the wafer using all or some of the stored altered output. In addition, the method may include determining one or more attributes of the non-spatially localized characteristic using all or some of the stored altered output for the wafer (e.g., an average value or some statistical value of the non-spatially localized characteristic across some portion of the wafer).

As described above, the characteristic(s) that are determined may include at least one non-spatially localized characteristic and at least one characteristic that is spatially localized in at least one dimension. Therefore, one advantage of the methods described herein is that the altered output can be used to detect both spatially localized characteristic(s) and non-spatially localized characteristic(s) of wafers. For example, the altered output may be used to detect both point defects on the wafer and to determine variations in surface roughness and/or film thickness on the wafer.

As shown in FIG. 1, the method may include reporting analysis and detection results, as shown in step 28. Reporting the analysis and detection results may be performed by displaying the results to a user in any suitable format.

It is noted that all of the steps shown in FIG. 1 are not essential to practice of the method. One or more steps may be omitted from or added to the method illustrated in FIG. 1, and the method can still be practiced within the scope of this embodiment. For example, for some specific applications, more processing stages can be added into this framework to provide additional services.

In one embodiment, the one or more characteristics include variations in background light scattering from the wafer. In one such embodiment, the method includes monitoring a process performed on the wafer based on the variations in the background tight scattering. One advantage of such monitoring is that relatively subtle signal variations in the background may be detected and quantified as a means of monitoring process variations (e.g., for statistical process control (SPC) to monitor an integrated circuit (IC) manufacturing process). Monitoring process variations can also be performed using any of the one or more characteristics of the wafer determined as described herein.

In another embodiment, the altered output includes a signal map for the wafer. In one such embodiment, the method includes detecting excursions in the signal map relative to signal maps for one or more other wafers in the same lot as the wafer or in a different lot than the wafer. The signal maps for one or more other wafers may also be generated as described herein. In this manner, the methods described herein may be used for comparing background inspection signals for improved surface anomaly detection.

The embodiments described herein may also include storing results of one or more steps of one or more computer-implemented methods described herein in a computer-readable medium. After the results have been stored, the results can be accessed in the computer-readable medium and used by any of the method or system embodiments described herein, any other method, or any other system. Furthermore, the results may be stored "permanently," "semi-permanently," temporarily, or for some period of time.

Each of the embodiments of the computer-implemented method described above may include any other step(s) of any other computer-implemented method embodiment(s) described herein. In addition, each of the embodiments of the computer-implemented method described above may be performed by any of the systems described herein.

Figure 5:
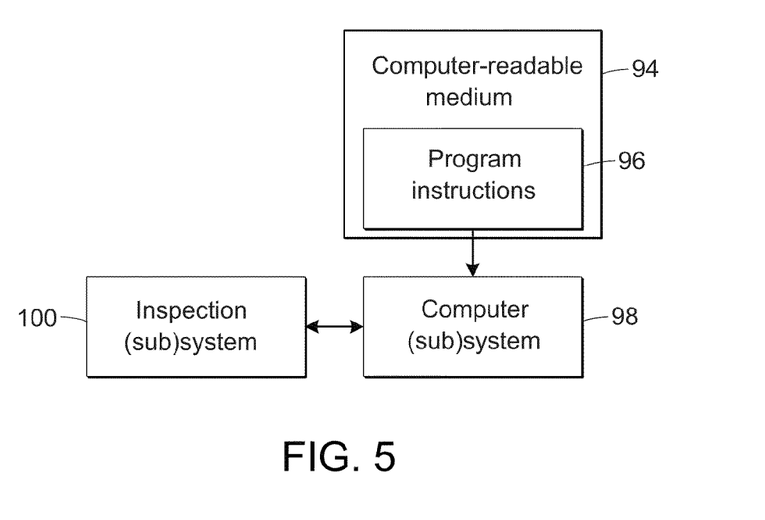
FIG. 5 is a block diagram illustrating one embodiment of a system configured to determine one or more characteristics of a wafer and one embodiment of a computer-readable medium storing program instructions executable on a computer system for performing one or more computer-implemented methods described herein.

Another embodiment relates to a computer-readable medium storing program instructions executable on a computer system for performing a computer-implemented method for determining one or more characteristics of a wafer. One such embodiment is shown in FIG. 5. For example, as shown in FIG. 5, computer-readable medium 94 stores program instructions 96 executable on computer system 98 for performing a computer-implemented method for determining one or more characteristics of a wafer.

The computer-implemented method includes performing the following steps using the computer system. The computer-implemented method includes acquiring output generated for the wafer by an inspection system, which may be performed as described herein. The computer-implemented method also includes separately altering the output generated for different locations on the wafer using a reference corresponding to the different locations on the wafer, which may be performed as described herein. The output that is altered may include any of the output described herein. The method further includes determining one or more characteristics of the wafer using the altered output, which may be performed as described herein.

Program instructions 96 implementing computer-implemented methods such as those described herein may be stored on computer-readable medium 94. The computer-readable medium may be anon-transitory computer-readable medium such as a computer-readable storage medium (e.g., a read-only memory, a RAM, a magnetic or optical disk, or a magnetic tape).

The program instructions may be implemented in any of various ways, including procedure-based techniques, component-based techniques, and/or object-oriented techniques, among others. For example, the program instructions may be implemented using Matlab, Visual Basic, ActiveX controls, C, C++, C++objects, C#, JavaBeans, Microsoft Foundation Classes ("MFC"), or other technologies, methodologies, or programming languages, as desired.

The computer system may take various forms, including a personal computer system, a digital signal processor (DSP), image computer, mainframe computer system, workstation, network appliance, Internet appliance, or other device. In general, the term "computer system" may be broadly defined to encompass any device having one or more processors, which executes instructions from a memory medium. In addition, the computer system may be included in or external to an inspection system (but coupled to the inspection system such that the computer system can acquire the output generated by the inspection system). The computer-implemented method for which the program instructions are executable may include any other step(s) of any other method(s) described herein FIG. 5 also illustrates one embodiment of a system configured to determine one or more characteristics of a wafer. The system includes inspection subsystem 100. The inspection subsystem is configured to generate output for the wafer. For example, the inspection subsystem may be configured to scan light over the wafer and detect light scattered and/or reflected from the wafer during the scan. In this manner, the inspection subsystem may be configured as a dark field (DF) and/or bright field (BF) inspection subsystem. The inspection subsystem may also be configured as described in U.S. Pat. No. 7,286,218 to Judell et al, and/or commonly owned U.S. patent application Ser. No. 12/128,426 by Biellak et al, filed May 28, 2008, which published as U.S. Patent Application Publication No. 2009/0299655 on Dec. 3, 2009, which are incorporated by reference as if fully set forth herein. Furthermore, the inspection subsystem may include an existing inspection subsystem such as the inspection subsystems included in the SPx series of tools, which are commercially available from KLA-Tencor. For some such systems, the functionality of the embodiments described herein may be provided as optional functionality of the system (e.g., in addition to other functionality of the system).

The system also includes computer subsystem 98. The computer subsystem is configured to acquire the output for the wafer generated by the inspection subsystem, which may be performed as described herein. The computer subsystem is also configured to separately alter the output generated for different locations on the wafer using a reference corresponding to the different locations on the wafer, which may be performed as described further herein. The output that is altered may include any of the output described herein. In addition, the computer subsystem is configured to determine one or more characteristics of the wafer using the altered output, which may be performed as described further herein. The computer subsystem may be configured to perform any other step(s) of any other computer-implemented method embodiment(s) described herein. In addition, the system may be configured to perform any other step(s) of any other computer-implemented method embodiment(s) described herein.

Further modifications and alternative embodiments of various aspects of the invention may be apparent to those skilled in the art in view of this description. For example, computer-implemented methods, computer-readable media, and systems for determining one or more characteristics of a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining one or more characteristics of a wafer, comprising:
   using a computer system to perform the steps of:
   acquiring output generated for the wafer by an inspection system;
   separately altering the output generated for different locations on the wafer using a reference corresponding to the different locations on the wafer, wherein the output that is altered comprises output that does not correspond to defects on the wafer; and
   determining one or more characteristics of the wafer using the altered output, wherein the one or more characteristics comprise at least one characteristic that is not spatially localized in two dimensions.

2. The method of claim 1, wherein the one or more characteristics further comprise at least one characteristic that is spatially localized in at least one dimension.

3. The method of claim 1, wherein said separately altering is performed prior to detecting the defects on the wafer, and wherein the defects are spatially localized in at least one dimension.

4. The method of claim 1, wherein the inspection system generates the output for the wafer by scanning the wafer during an inspection process, and wherein the reference is created from additional output generated by scanning the wafer with the inspection system during the inspection process.

5. The method of claim 1, wherein the inspection system generates the output for the wafer by scanning the wafer during an inspection process, and wherein the reference is created from additional output generated by scanning the wafer with the inspection system or a different inspection system during a different process.

6. The method of claim 1, wherein the inspection system generates the output for the wafer by scanning the wafer during an inspection process, and wherein the reference is created from additional output generated by scanning a different wafer with the inspection system or a different inspection system.

7. The method of claim 1, wherein the inspection system generates the output for the wafer by scanning the wafer during an inspection process, wherein the reference is created from additional output generated by scanning a different wafer with the inspection system or a different inspection system, and wherein the wafer and the different wafer are in the same lot.

8. The method of claim 1, wherein the inspection system generates the output for the wafer by scanning the wafer during an inspection process, wherein the reference is created from additional output generated by scanning a different wafer with the inspection system or a different inspection system, and wherein the wafer and the different wafer are in different lots.

9. The method of claim 1, further comprising determining a derivative of the output generated for the wafer, wherein the reference comprises a derivative of different output generated by scanning the wafer or a different wafer with the inspection system or a different inspection system, and wherein said separately altering comprises separately altering the derivative of the output generated for the different locations using the derivative of the different output corresponding to the different locations.

10. The method of claim 1, wherein the reference is created by performing a function on data acquired from a computer-readable medium.

11. The method of claim 1, wherein the reference is created by performing a function on data generated for two or more wafers by one or more inspection systems.

12. The method of claim 1, wherein the reference comprises a map of reference values corresponding to the different locations on the wafer.

13. The method of claim 1, wherein the altered output comprises a map of values corresponding to the different locations on the wafer.

14. The method of claim 1, wherein said separately altering suppresses background and surface features in the output.

15. The method of claim 1, wherein said determining comprises extracting one or more features of the wafer from the altered output.

16. The method of claim 1, wherein the one or more characteristics further comprise variations in background light scattering from the wafer, and wherein the method further comprises monitoring a process performed on the wafer based on the variations in the background light scattering.

17. The method of claim 1, wherein the altered output comprises a signal map for the wafer, and wherein the method further comprises detecting excursions in the signal map relative to signal maps for one or more other wafers in the same lot as the wafer or in a different lot than the water.

18. A non-transitory computer-readable medium storing program instructions executable on a computer system for performing a computer-implemented method for determining one or more characteristics of a wafer, wherein the computer-implemented method comprises:

using the computer system to perform the steps of:

acquiring output generated for the wafer by an inspection system;

separately altering the output generated for different locations on the wafer using a reference corresponding to the different locations on the wafer, wherein the output that is altered comprises output that does not correspond to defects on the wafer; and determining one or more characteristics of the wafer using the altered output, wherein the one or more characteristics comprise at least one characteristic that is not spatially localized in two dimensions.

19. A system configured to determine one or more characteristics of a wafer, comprising:

an inspection subsystem configured to generate output for the wafer; and a computer subsystem configured to:

acquire the output;

separately alter the output generated for different locations on the wafer using a reference corresponding to the different locations on the wafer, wherein the output that is altered comprises output that does not correspond to defects on the wafer; and determine one or more characteristics of the wafer using the altered output, wherein the one or more characteristics comprise at least one characteristic that is not spatially localized in two dimensions.

* * * * *